(12) United States Patent
Alman et al.

(10) Patent No.: US 10,722,493 B2
(45) Date of Patent: *Jul. 28, 2020

(54) METHODS FOR TREATING FIBROPROLIFERATIVE DISORDERS IN A MAMMAL

(71) Applicant: Hospital For Sick Children, Toronto (CA)

(72) Inventors: Benjamin A. Alman, Toronto (CA); Raymond Poon, Toronto (CA); Helen Hong, Toronto (CA); Gene Gauzer, Kirkland (CA)

(73) Assignee: The Hospital for Special Children, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,516

(22) Filed: May 19, 2017

(65) Prior Publication Data

US 2017/0281594 A1 Oct. 5, 2017

Related U.S. Application Data

(63) Continuation of application No. 15/390,468, filed on Dec. 24, 2016, now abandoned, which is a continuation of application No. 14/577,329, filed on Dec. 19, 2014, now Pat. No. 9,566,263, which is a continuation-in-part of application No. 13/516,016, filed on Jun. 14, 2012, now Pat. No. 8,957,107.

(60) Provisional application No. 61/286,533, filed on Dec. 15, 2009.

(51) Int. Cl.
| | | |
|---|---|---|
| *A61K 31/395* | (2006.01) |
| *A61K 9/06* | (2006.01) |
| *A61K 9/00* | (2006.01) |
| *A61K 31/191* | (2006.01) |
| *A61K 47/10* | (2017.01) |
| *A61K 31/235* | (2006.01) |
| *A61K 47/14* | (2017.01) |
| *A61K 47/18* | (2017.01) |

(52) U.S. Cl.
CPC .......... *A61K 31/395* (2013.01); *A61K 9/0014* (2013.01); *A61K 9/06* (2013.01); *A61K 31/191* (2013.01); *A61K 31/235* (2013.01); *A61K 47/10* (2013.01); *A61K 47/14* (2013.01); *A61K 47/183* (2013.01)

(58) Field of Classification Search
CPC ...... A61K 31/395; A61K 47/10; A61K 47/14; A61K 9/06; A61K 9/0014; A61K 31/235; A61K 47/183; A61K 31/191; A61K 47/38; A61K 31/5545; A61P 17/02
See application file for complete search history.

(56) References Cited

U.S. PATENT DOCUMENTS

| | | | | |
|---|---|---|---|---|
| 8,957,107 B2* | 2/2015 | Alman | ................ | A61K 31/395 424/445 |
| 2006/0040905 A1* | 2/2006 | Lyne | .................. | A61K 31/395 514/183 |

OTHER PUBLICATIONS

Pulmonary Fibrosis, [online]. Mayo Clinic, 2019 [retrieved on Feb. 6, 2019]. Retrieved from the Internet: URL:https://www.mayoclinic.org/diseases-conditions/pulmonary-fibrosis/symptoms-causes/syc-20353690>, 11 pages (Year: 2019).*

Bataller, R., Liver Fibrosis, Feb. 2005, The Journal of Clinical Investigation, vol. 115, No. 2, pp. 209-218. (Year: 2005).*

* cited by examiner

*Primary Examiner* — Sue X Liu
*Assistant Examiner* — Andriae M Holt

(57) ABSTRACT

Methods of treating fibroproliferative disorders mediated by β-catenin in mammals, including aggressive fibromatoses, also called desmoid tumour.

4 Claims, 10 Drawing Sheets

METHODS FOR TREATING FIBROPROLIFERATIVE DISORDERS IN A MAMMAL

CROSS REFERENCE TO RELATED APPLICATIONS

This application is a continuation-in-part of U.S. patent application Ser. No. 13/516,016 filed on Dec. 15, 2010 which claims priority to U.S. Provisional Application Ser. No. 61/286,633, filed Dec. 15, 2009, the contents of which are incorporated herein by reference.

FIELD OF THE INVENTION

The present invention generally relates to the treatment of scars and ε-catenin-mediated disorders.

BACKGROUND OF THE INVENTION

Fibroproliferative processes are a group of disorders characterized by an excessive proliferation of mesenchymal fibroblast-like spindle cells. They range from hypertrophic wounds to the development of neoplasms such as aggressive fibromatosis (AF).

During wound healing, several cell types and signaling pathways are activated to reconstitute the epithelial and dermis layers of the skin. Following cutaneous injury, three sequentially distinct but overlapping processes are initiated: inflammatory, proliferation, and remodeling. During the proliferative phase, mesenchymal fibroblast-like cells accumulate in the dermal component of the skin while the epithelial cell barrier layer is reformed (Singer 1999, Martin 1997, McClain 1996). β-catenin has been shown to mediate epithelial and mesenchymal cell activity, whereby it is able to increase proliferation and differentiation in dermal mesenchymal cells and decrease migration in epithelial keratinocytes (Cheon 2002). Mouse models have demonstrated that β-catenin can modulate the resulting wound size, where induced levels of β-catenin by lithium treatment result in wound healing with a larger size (Cheon 2006). Also, a transgenic mouse in which stabilized β-catenin is expressed in mesenchymal cells, has been generated, under control of a tetracycline-regulated promoter. Wounded mice healed with hyperplastic cutaneous wounds compared to wildtype control mice (Cheon 2002). This demonstrates the importance of β-catenin in mesenchymal cells and its crucial role in wound healing.

Another fibroproliferative disorder mediated by β-catenin is aggressive fibromatosis (AF), also called desmoid tumour. AF is a locally invasive soft tissue tumour comprised of mesenchymal fibroblast-like spindle cells. AF occurs as either a sporadic lesion or a familial syndrome, such as familial adenomatous polyposis (FAP). B-catenin stabilization is a universal occurrence in AF, as demonstrated by elevated β-catenin levels and increase β-catenin-mediated transcriptional activity. Furthermore, β-catenin stabilization is sufficient to cause AF as shown using a transgenic mouse model that over-expresses the stabilized form of β-catenin (Cheon 2002). This suggests a crucial role β-catenin plays in fibroproliferative disorders and its importance in mesenchymal cells.

In addition to a role for β-catenin in fibroproliferative disorders, a number of studies have demonstrated deregulated β-catenin expression is an important event in the genesis of a number of malignancies, such as colon cancer, melanoma, hepatocellular carcinoma, ovarian cancer, endometrial cancer, medulloblastoma pilomatricomas, and prostate cancer. β-catenin mutations appear to be a crucial step in the progression of a subset of these cancers, suggesting an important role in the control of cellular proliferation or cell death (as described in Polakis P. The many ways of Wnt in cancer. Curr Opin Genet Dev. 2007 February; 17(1):45-51).

In view of foregoing, it is desirable to develop novel methods effective to treat conditions and disorders that may be associated with β-catenin.

SUMMARY OF THE INVENTION

It has now been found that Nefopam, and analogues thereof, are useful to treat disorders mediated by β-catenin, such as fibroproliferative disorders, as well as treating scar tissue.

Accordingly, in one aspect of the invention, a topical formulation of Nefopam is encompassed, comprising a compound selected from Nefopam or a functionally equivalent salt or solvate thereof; at least one fatty alcohol emulsifier selected from the group consisting of cetyl alcohol and stearyl alcohol; an oil-in water emulsifier; at least one preservative; at least one penetration enhancer selected from the group consisting of diethylene glycol monoethyl and isopropyl myristate; and sodium hydroxide.

In another aspect, the invention encompasses methods of reducing the size of a dermal scar comprising providing a topical drug formulation twice per day beginning on about day 5 to about day 7 following wounding, wherein the formulation comprises one percent Nefopam HCl, emulsifiers, at least one penetration enhancer, and at least one preservative, and further comprises a pH of about 5.3.

BRIEF DESCRIPTION OF THE DRAWINGS

The present invention will now be described in further detail with reference to the following Figures.

DETAILED DESCRIPTION OF THE PREFERRED EMBODIMENTS

Figure 1A:
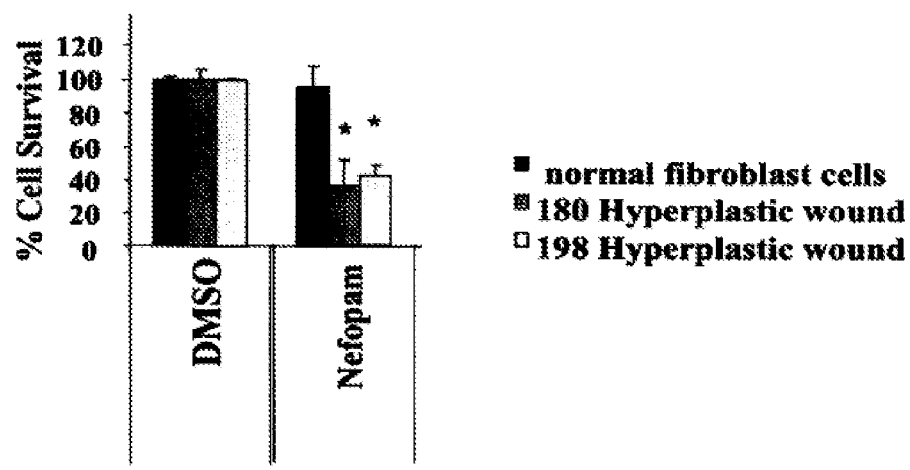
FIG. 1A is a bar graph indicating cell viability in cultured normal fibroblast cells and cultured cells derived from two hyperplastic wounds following treatment with DMSO (control) or Nefopam using the SRB assay. Percent cell survival is given as a mean and 95% confidence interval. There is significant decline in the percent of cells surviving in cultures treated with Nefopam compared to DMSO control hyperplastic wound cell cultures, however, cell survival rates in normal fibroblast cultures remained relatively unchanged (asterisk indicates significance compared to normal fibroblast cultures).

A method of treating a β-catenin-mediated disorder in a mammal is provided comprising administering Nefopam or a functionally equivalent analogue thereof to the mammal.

As used herein, the term "β-catenin-mediated disorder or condition" refers to disorders or conditions characterized by the accumulation of fibrous tissue ("fibrosis") including, but not limited to, fibroproliferative disorders such as dermal scars including hypertrophic, hyperplastic and keloid scars, either in formation or already formed, and aggressive fibromatoses e.g. sporadic lesion or a familial syndrome such as familial adenomatous polyposis (FAP), liver fibrosis, lung fibrosis (e.g., silicosis, asbestosis), kidney fibrosis (including diabetic nephropathy), glomerulosclerosis, Lederhose disease and Dupuytren's contracture (DC), as well as malignancies, such as colon cancer, colorectal cancer, melanoma, hepatocellular carcinoma, ovarian cancer, endometrial cancer, medulloblastoma pilomatricomas, and prostate cancer.

The term "Nefopam" refers to 5-methyl-1-phenyl-1,3,4,6-tetrahydro-2,5-benzoxazocine and pharmaceutically acceptable functionally equivalent analogues, prodrugs, salts and solvates thereof. The term "functionally equivalent", as it used with respect to analogues, prodrugs, salts and solvates of Nefopam, refers to the ability of the selected compound to modulate β-catenin. The extent to which the selected compound may modulate β-catenin may vary from compound to compound.

The term "analogue" as used herein refers to compounds having the following general formula (1),

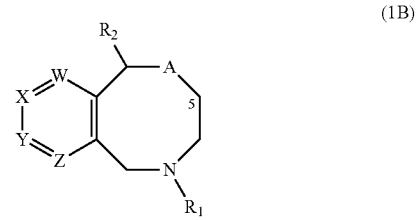

(1B)

wherein $R_1$ is H, $C_1$-$C_6$ alkyl optionally substituted with F or $C_3$-$C_6$cycloalkyl or $C_2$-$C_4$alkenyl; A is O, $CH_2$ or $S(O)_n$ where n is 0-2; one of W, X, Y and Z is N, CH or $CR_3$ and the others are CH; $R_2$ is $C_5$-$C_6$ heteroaryl, $C_5$-$C_10$ cycloalkyl or cycloalkenyl optionally containing one or more heteroatoms selected from O, N and $S(O)_n$ where n is 0-2, and optionally substituted with $R_3$; or a phenyl group optionally substituted in one or more positions with one or more substituents independently selected from halogen, CN, CF$_3$, C$_1$-C$_6$ alkyl and OR$_1$, or the phenyl group is fused to a five or six membered ring which may be carbocyclic, heterocyclic (containing 1-2 heteroatoms selected from O, N and S), aromatic or heteroaromatic (containing 1-2 heteroatoms selected from O and N); R$_3$ is selected from halogen; CF$_3$; CN; OR$_5$; SO$_2$N(R$_5$)$_2$; COR$_5$; CO$_2$R$_5$; CON(R$_5$)$_2$; NR$_1$COR$_4$; NR$_1$SO$_2$R$_4$; NR$_1$CO$_2$R$_4$; NR$_1$CON(R$_5$)$_2$; OC$_1$-C$_6$ alkyl substituted with R$_3$; C$_1$-C$_6$ alkyl optionally substituted with unsubstituted R$_3$; C$_3$-C$_6$cycloalkyl optionally substituted with unsubstituted R$_3$; C$_2$-C$_6$alkenyl optionally substituted with unsubstituted R$_3$; C$_2$-C$_6$alkynyl optionally substituted with unsubstituted R$_3$; aryl optionally substituted with unsubstituted R$_3$; and five or six membered aromatic heterocycles containing 1-4 heteroatoms selected from N and O; R$_4$ is C$_1$-C$_6$ alkyl, C$_2$-C$_6$alkenyl, C$_2$-C$_6$alkynyl, C$_3$-C$_6$cycloalkyl, aryl or heteroaryl; and R$_5$ is H, C$_1$-C$_6$ alkyl, C$_2$-C$_6$alkenyl, C$_2$-C$_6$alkynyl, C$_3$-C$_6$cycloalkyl, aryl or heteroaryl and is the same as or different to another R$_5$; or a pharmaceutically acceptable salt thereof; wherein R$_1$ is H, C$_1$-C$_6$ alkyl, optionally substituted with F or C$_3$-C$_6$cycloalkyl or C$_2$-C$_6$ alkenyl; R$_2$ and R$_3$ are the same or different and are H, a halogen, CN, CF$_3$, C$_1$-C$_6$ alkyl or OR$_1$, or R$_2$ and R$_3$ form a five or six membered ring which may be carbocyclic, heterocyclic (containing 1-2 heteroatoms taken from O, N and S), aromatic or heteroaromatic (containing 1-2 heteroatoms taken from O and N); one of W, X, Y and Z is N, or CR$_4$ and the others are each CH; R$_4$ is a halogen atom, CF$_3$, CN, OR$_7$, SO$_2$N(R$_6$)$_2$, COR$_2$, CO$_2$R$_6$, CON(R$_6$)$_2$, NR$_1$COR$_5$, NR$_1$SO$_2$R$_5$, NR$_1$CO$_2$R$_5$, NR$_1$CON(R$_6$)$_2$, OC$_1$-C$_6$ alkyl optionally substituted with R$_4$, C$_1$-C$_6$ alkyl optionally substituted with R$_4$, C$_3$-C$_6$cycloalkyl optionally substituted with R$_4$, C$_2$-C$_6$alkenyl optionally substituted with R$_4$, C$_2$-C$_6$alkynyl optionally substituted with R$_4$, aryl optionally substituted with R$_4$, or a five or six membered aromatic heterocycle containing 1-4 heteroatoms selected from N and O, linked either through carbon or nitrogen; R$_5$ is C$_1$-C$_6$ alkyl, C$_2$-C$_6$alkenyl, C$_2$-C$_6$alkynyl, C$_3$-C$_6$cycloalkyl, aryl or heteroaryl; each R$_6$ (which may be the same or different) is H, C$_1$-C$_6$ alkyl, C$_2$-C$_6$alkenyl, C$_2$-C$_6$alkynyl, C$_3$-C$_6$cycloalkyl, aryl or heteroaryl; and R$_7$ is aryl or heteroaryl; or a pharmaceutically acceptable salt thereof; wherein R$_1$ is H, C$_1$-C$_6$ alkyl optionally substituted with F or C$_3$-C$_6$cycloalkyl or C$_2$-C$_4$alkenyl; A is O, CH$_2$ or S(O)$_n$ where n is 0-2; one of W, X, Y and Z is N, CH or CR$_3$ and the others are CH; R$_2$ is C$_5$-C$_6$heteroaryl, C$_5$-C$_{10}$ cycloalkyl or cycloalkenyl optionally containing one or more heteroatoms selected from O, N and S(O)$_n$ where n is 0-2, and optionally substituted with R$_3$; or a phenyl group optionally substituted in one or more positions with one or more substituents independently selected from halogen, CN, CF$_3$, C$_1$-C$_6$ alkyl and OR$_1$, or the phenyl group is fused to a five or six membered ring which may be carbocyclic, heterocyclic (containing 1-2 heteroatoms selected from O, N and S), aromatic or heteroaromatic (containing 1-2 heteroatoms selected from O and N); R$_3$ is selected from halogen; CF$_3$; CN; OR$_5$; SO$_2$N(R$_5$)$_2$; COR$_5$; CO$_2$R$_5$; CON(R$_5$)$_2$; NR$_1$COR$_4$; NR$_1$SO$_2$R$_4$; NR$_1$CO$_2$R$_4$; NR$_1$CON(R$_5$)$_2$; OC$_1$-C$_6$ alkyl substituted with R$_3$; C$_1$-C$_6$ alkyl optionally substituted with unsubstituted R$_3$; C$_3$-C$_6$cycloalkyl optionally substituted with unsubstituted R$_3$; C$_2$-C$_6$alkenyl optionally substituted with unsubstituted R$_3$; C$_2$-C$_6$alkynyl optionally substituted with unsubstituted R$_3$; aryl optionally substituted with unsubstituted R$_3$; and five or six membered aromatic heterocycles containing 1-4 heteroatoms selected from N and O; R$_4$ is C$_1$-C$_6$ alkyl, C$_2$-C$_6$alkenyl, C$_2$-C$_6$alkynyl, C$_3$-C$_6$cycloalkyl, aryl or heteroaryl; and R$_5$ is H, C$_1$-C$_6$ alkyl, C$_2$-C$_6$alkenyl, C$_2$-C$_6$alkynyl, C$_3$-C$_6$cycloalkyl, aryl or heteroaryl and is the same as or different to another R$_5$; or a pharmaceutically acceptable salt thereof; wherein R$_1$ is H, C$_1$-C$_6$ alkyl optionally substituted with F or C$_3$-C$_6$cycloalkyl or C$_2$-C$_4$alkenyl; A is O, CH$_2$ or S(O)$_n$ where n is 0-2; one of W, X, Y and Z is N, CH or CR$_3$ and the others are CH; R$_2$ is C$_5$-C$_6$ heteroaryl, C$_5$-C$_{10}$ cycloalkyl or cycloalkenyl optionally containing one or more heteroatoms selected from O, N and S(O)$_n$ where n is 0-2, and optionally substituted with R$_3$; or a phenyl group optionally substituted in one or more positions with one or more substituents independently selected from halogen, CN, CF$_3$, C$_1$-C$_6$ alkyl and OR$_1$, or the phenyl group is fused to a five or six membered ring which may be carbocyclic, heterocyclic (containing 1-2 heteroatoms selected from O, N and S), aromatic or heteroaromatic (containing 1-2 heteroatoms selected from O and N); R$_3$ is selected from halogen; CF$_3$; CN; OR$_5$; SO$_2$N(R$_5$)$_2$; COR$_5$; CO$_2$R$_5$; CON(R$_5$)$_2$; NR$_1$COR$_4$; NR$_1$SO$_2$; NR$_1$CO$_2$R$_4$; NR$_1$CON(R$_5$)$_2$; OC$_1$-C$_6$ alkyl substituted with R$_3$; C$_1$-C$_6$ alkyl optionally substituted with unsubstituted R$_3$; C$_3$-C$_6$cycloalkyl optionally substituted with unsubstituted R$_3$; C$_2$-C$_6$alkenyl optionally substituted with unsubstituted R$_3$; C$_2$-C$_6$alkynyl optionally substituted with unsubstituted R$_3$; aryl optionally substituted with unsubstituted R$_3$; and five or six membered aromatic heterocycles containing 1-4 heteroatoms selected from N and O; R$_4$ is C$_1$-C$_6$ alkyl, C$_2$-C$_6$alkenyl, C$_2$-C$_6$alkynyl, C$_3$-C$_6$cycloalkyl, aryl or heteroaryl; and R$_5$ is H, C$_1$-C$_6$ alkyl, C$_2$-C$_6$alkenyl, C$_2$-C$_6$alkynyl, C$_3$-C$_6$cycloalkyl, aryl or heteroaryl and is the same as or different to another R$_5$; or a pharmaceutically acceptable salt thereof; or wherein: R$_1$ is H, C$_1$-C$_6$ alkyl, optionally substituted with F or C$_3$-C$_6$ cycloalkyl or C$_2$-C$_4$ alkenyl; R$_2$ and R$_3$ are the same or different and are each H, halogen, CN, CF$_3$, C$_1$-C$_6$ alkyl or OR$_1$, or R$_2$ and R$_3$ may form a five or six membered ring which may be carbocyclic, heterocyclic (containing 1-2 heteroatoms taken from O, N and S), aromatic or heteroaromatic (containing 1-2 heteroatoms taken from O and N); and one of W, X, Y and Z is N, CH or CR$_4$ and the others are CH; R$_4$ is halogen; CF$_3$; CN; OR$_7$; SO$_2$N(R$_6$)$_2$ (where each R$_6$ is the same or different); COR$_2$; CO$_2$R$_6$; CON(R$_6$)$_2$ (where R$_6$ is the same or different); NR$_1$COR$_5$; NR$_1$SO$_2$R$_5$; NR$_1$CO$_2$R$_5$; NR$_1$CON(R$_6$)$_2$ (where each R$_6$ is the same or different), OC$_1$-C$_6$ alkyl substituted with unsubstituted R$_4$, C$_1$-C$_6$ alkyl optionally substituted with unsubstituted R$_4$, C$_3$-C$_6$cycloalkyl optionally substituted with unsubstituted R$_4$, C$_2$-C$_6$alkenyl optionally substituted with unsubstituted R$_4$, C$_2$-C$_6$alkynyl optionally substituted with unsubstituted R$_4$ and aryl optionally substituted with unsubstituted R$_4$, or R$_4$ is a five or six membered aromatic heterocycle containing 1-4 heteroatoms taken from N and O; R$_5$ is C$_1$-C$_6$alkyl, C$_2$-C$_6$alkenyl, C$_2$-C$_6$alkynyl, C$_3$-C$_6$cycloalkyl, aryl or heteroaryl; R$_6$ can be H, C$_1$-C$_6$alkyl, C$_2$-C$_6$alkenyl, C$_2$-C$_6$alkynyl, C$_3$-C$_6$cycloalkyl, aryl or heteroaryl; and R$_7$ is aryl or heteroaryl; or a pharmaceutically acceptable salt thereof. Additional analogues of Nefopam are described in WO2004/056788, WO2005/103019 and US2006/0019940, the contents of which are incorporated herein by reference. Nefopam and analogues thereof may be made using chemical synthetic methods well-known to those in the art. In addition, Nefopam is commercially available.

The term "prodrug" refers to a compound (e.g. a drug precursor) that is transformed in vivo to yield a compound having the structure of Nefopam or a pharmaceutically acceptable analogue, salt, hydrate or solvate thereof. The transformation may occur by various mechanisms (e.g., by metabolic or chemical processes), such as, for example, through hydrolysis in blood. The term "salt(s)", as employed herein, denotes acidic salts formed with inorganic and/or organic acids, as well as basic salts formed with inorganic and/or organic bases. Pharmaceutically acceptable (i.e., non-toxic, physiologically acceptable) salts are preferred, although other salts are also useful. A "solvate" is formed by admixture of Nefopam or an analogue thereof in a solvent which is preferably pharmaceutically acceptable.

The present method encompasses the treatment of a β-catenin-mediated disorder in a mammal. The terms "treat", "treating" and "treatment" are used broadly herein to denote methods that favorably alter the targeted disorder, including those that moderate or reverse the progression of, reduce the severity of, or prevent, the disorder. The term "mammal" is used herein to encompass both human and non-human mammals.

A method of treating dermal scars, including scars resulting from cuts, scrapes, infection, acne, burns, surgery, etc., hypertrophic, hyperplastic, keloid, scars involving mesenchymal and mesenchymal-derived cells, any of which may be β-catenin-mediated or not, is also provided. The method comprises administering to the target site a therapeutically effective amount of a Nefopam compound. The method of treating scars, in formation or already formed, includes reducing the size of the scar (for example, by at least about 5-10%, preferably by at least about 20%, and more preferably by at least about 25% or more) or prevalence of the scar (e.g. elevation of the scar, redness, etc.) and thereby improving the appearance thereof. In this regard, as one of skill will appreciate, a scar assessment scale, e.g. the Manchester Scale, may be used to assess the improvement of a given scar. The Manchester Scale assesses colour compared with surrounding skin, matte or shiny appearance, contour (flush with surrounding skin to scar/keloid), texture (normal to hard), margins (distinct or not), size and number (single or multiple) (Disability & Rehabilitation, 2009, Vol. 31, No. 25: Pages 2055-2063; *International Journal of Lower Extremity Wounds December* 2007 6: 249-253).

Thus, Nefopam compounds may be utilized in a cosmetic treatment to reduce scar tissue and improve the aesthetics of the scar and surrounding area, and may provide additional cosmetic features, e.g. anti-wrinkling effects.

In another embodiment, a method of treating tumours is provided. Tumour treatment includes inhibiting tumour initiation and tumour cell proliferation. The method is useful to treat tumours resulting from deregulated β-catenin expression such as aggressive fibromatosis, as well as tumours resulting from various cancers such as colon cancer, melanoma, hepatocellular cancer, ovarian cancer, endometrial cancer and prostate cancer. The method comprises administering to a mammal in need of treatment, i.e. a mammal having a tumour, an effective amount of Nefopam, an analogue thereof, or a pharmaceutically acceptable salt, solvate or prodrug thereof.

While not wishing to be bound by any particular theory, treatment in accordance with the present invention may be effected by the regulation or modulation of β-catenin expression, at the nucleic acid level, or the regulation or modulation of β-catenin activity, at the protein level.

Therapeutically effective dosages of Nefopam are administered to a mammal in accordance with the invention. The term "therapeutically effective" as it is used herein with respect to dosages refers to a dosage that is effective to treat a β-catenin-mediated disorder without causing unacceptable adverse side effects. The term "administered" refers to any appropriate means of providing Nefopam to a mammal, and will depend on the dosage form being used as will be described. For example, the dosage may be administered orally, by injection, mucosally and topically as will be described in more detail.

Therapeutically effective dosages according to the method, thus, are in the range of about 0.0001 to about 1500 mg, for example, in a range of about 0.0001-100 mg. However, as one of skill in the art will appreciate, the effective therapeutic dosage of Nefopam, or analogues thereof, will vary depending many factors, including but not limited to, the type of disorder to be treated, the nature and severity of the disorder, the mammal to be treated, the symptoms of the mammal being treated, the compound used for the treatment, and the route of administration.

Nefopam may be administered in accordance with methods of the invention alone or in a composition combined with a pharmaceutically acceptable adjuvant or carrier. The expression "pharmaceutically acceptable" means acceptable for use in the pharmaceutical arts, i.e. not being unacceptably toxic, or otherwise unsuitable for administration to a mammal. Examples of pharmaceutically acceptable adjuvants include, but are not limited to, diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule, lozenge, solution or suspension in an aqueous or non-aqueous liquid, an oil-in-water or water-in-oil liquid emulsion, an elixir or syrup are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, disintegrating agents, anti-oxidants, preservatives, colouring agents and flavouring agents may also be present. In another embodiment, the composition may be formulated for application topically as a cream, lotion or ointment. For such topical application, the composition may include an appropriate base such as a triglyceride base. Such creams, lotions and ointments may also contain a surface active agent and other cosmetic additives such as skin softeners and the like as well as fragrance. Aerosol formulations, for example, for nasal delivery, may also be prepared in which suitable propellant adjuvants are used. Compositions of the present invention may also be administered as a bolus, electuary, or paste. Compositions for mucosal administration are also encompassed, including oral, nasal, rectal or vaginal administration for the treatment of infections which affect these areas. Such compositions generally include one or more suitable non-irritating excipients or carriers comprising, for example, cocoa butter, polyethylene glycol, a suppository wax, a salicylate or other suitable carriers. Other adjuvants may also be added to the composition regardless of how it is to be administered which, for example, may aid to extend the shelf-life thereof.

In accordance with the present method, a Nefopam compound may be administered in a convenient manner by any of a number of routes including but not limited to oral, subcutaneous, intravenous, intraperitoneal, intranasal, enteral, topical, sublingual, intramuscular, intra-arterial, intramedullary, intrathecal, inhalation, ocular, transdermal, vaginal or rectal means. Nefopam compounds may also be administered to cells in ex vivo treatment protocols. Depending on the route of administration, Nefopam compounds may be coated or encased in a protective material to prevent degradation by, e.g. enzymes, acids or other conditions that may affect the therapeutic activity thereof.

In one embodiment, Nefopam, or an analogue thereof, may be topically applied to a target site, e.g. a scar in formation or already formed, affixed to a biocompatible device, polymer or other matrix, e.g. such as a bandage, dressing, polymer mesh, implant, device or other cosmetically related item. Dermal fibroblasts/keratinocytes bioengineered to express a Nefopam compound may also be applied to a target site. A suitable matrix or polymer mesh, e.g. artificial or non-artificial skin grafts, may alternatively be impregnated with a Nefopam compound for application to a target site to permit slow-release of the compound for continuous treatment of the site over a period of time.

Formulation of topical embodiments of the invention require the use of solvents, solubilizers, emulsifiers, thickening agents, dispersants, preservatives, buffers, chelating agents, and penetrating agents.

In certain topical embodiments of the invention Transcutol® P is used. It is a diethylene glycol monoethyl ether solvent and that is also as a solubilizer for poorly water-soluble active pharmaceutical ingredients. It is used to achieve improved drug penetration, permeation and a drug depot effect.

In certain topical embodiments of the invention, fatty alcohols such as cetyl alcohol and stearyl alcohol, are used as an emulsifier and thickening agent.

Topical embodiments may also contain Liposorb® S-20 (Polysorbate 60 NF) as an oil-in-water emulsifier to produce a fine-textured cream. Liposorb® S-20 also adds water-dispersibility and is a solubilizer.

Propyl Paraben NF may be used in embodiments of the invention as a preservative. This is particularly important in topical embodiments of the invention to be applied by patients on an out-patient basis.

Lexol® IPM-NF is a high purity isopropyl myristate solvent for topical use. In certain embodiments of the invention it improves penetration. The low odor and light color makes it ideal for topical embodiments of the invention where high emollient concentrations are required. It has a low viscosity, low freezing point, and good spreading properties. In certain embodiments Lexol® also enhances fluidity during cold storage and depress the cloud point of the formulation.

Methylparaben NF is a natural anti-fungal agent used in certain topical embodiments of the invention. It is a fine white, powder, odorless and soluble in water.

VERSEN NF (EDTA or ethylenediaminetetraacetic acid) is a chelating agent used in certain topical embodiments of the invention that provides metal ion control and is used for stabilization, helping to maintain potency of the Nefopam.

In some embodiments sodium hydroxide may be used for pH adjustment to achieve the desired pH of 5.0 to 5.6.

The present Nefopam compounds may be administered in a controlled release formulation using well-established methods including, for example, by dissolution or diffusion-controlled monolithic devices, beaded encapsulated systems, osmotically controlled systems, and modified film coating systems incorporating suitable polymeric and non-polymeric hydrophilic and hydrophobic materials. Suitable controlled-release formulations may include hydrophilic materials comprising, but not limited to, acrylic or methacrylic polymers or copolymers, alkylvinyl polymers, celluloses, hydroxyalkyl celluloses, carboxyalkyl celluloses, polysaccharides, alginates, pectins, starches and derivatives, natural and synthetic gums, polycarbophil, chitosans. Suitable hydrophobic materials comprise, but are not limited to, hydrophobic polymers, waxes, fats, long-chained fatty acids, their corresponding esters, their corresponding ethers, and their mixtures.

In another embodiment, Nefopam compounds may be administered in combination with one or more additional therapeutic agents, including for example, an anti-scarring agent; a wound healing agent such as a growth factor, e.g. epidermal growth factor, bFGF, PDGF; platelets, dermal fibroblasts and keratinocytes; chemotherapeutic agents such as, but not limited to, rapamycin, troglitazone, rosiglitazone, celecoxib, retinoids and iressa. In this regard, Nefopam may be administered in a separate formulation, or together with an additional therapeutic agent in a combined formulation.

The stimulation of the calcium stimulating receptor, CaSR, by $Ca^{2+}$ produced a striking and time-dependent decrease in the phosphorylation that promotes β-catenin transcriptional activity. The reduced phosphorylation of β-catenin coincides with a decline in its nuclear localization and a marked redistribution to the plasma membrane. Furthermore, CaSR stimulation by $Ca^{2+}$ promoted a down-regulation of β-catenin-mediated transcriptional activation. Thus, in certain embodiments of the invention, $Ca^{2+}$ may be added to the drug form to enhance the β-catenin inhibiting activity of Nefopam (The Journal of Biological Chemistry, 287, 1158-1167 (2012)). Various forms of calcium may be employed including calcium gluconate NF.

In addition, the present methods may be utilized in a combination with other therapies, for example, in combination with radiation therapy in the treatment of malignancies, or in combination with laser therapy to treat scar tissue such as normal scars, hyperplastic scar tissue and the like.

In a further aspect of the invention, an article of manufacture is provided comprising packaging and a composition comprising Nefopam as described. The packaging is labelled to indicate that the composition is suitable to treat a β-catenin-mediated disorder, or may be labelled to indicate that the composition is suitable to treat scarring, either in formation or already formed.

The present invention is described by reference to the accompanying Figures and specific examples which are not to be construed as limiting.

EXAMPLES

The following materials and methods were used in the examples discussed below.

$Apc^+/Apc^{1638N}$ AF Mouse Model and Treatment Plan.

The generation and phenotype of Apc/Apc1638N mice have been well characterized. These mice harbour a targeted mutation at codon 1638 in the Apc gene as a result of a neomycin insert in antisense orientation at exon 15. Male mice develop an average of 45 AF lesions and 6 gastrointestinal polyps by the age of 6 months, while female mice develop significantly fewer numbers of AF lesions. Male Apc/Apc1638N mice were divided into three study groups: No Treatment (n=11), 0.1% DMSO (n=10), and Nefopam at 40 mg/kg body weight (n=10). Treatment by daily oral gavaging began 2 months after Apc/Apc1638N mice were weaned and continued for 3 months. At autopsy, AF tumours and intestinal polyps were scored macroscopically. AF tumours and normal tissue were collected for protein extraction and fixed for histological examination.

Tcf Reporter Mice and Wounding Experiments.

A Tcf-reporter construct containing the lacZ gene downstream of a c-Fos minimal promoter and three consensus Tcf-binding motifs was constructed. Upon binding of β-catenin/Tcf complex to Tcf motifs, the expression of lacZ is activated. Tcf mice were wounded as described previously: two 4 mm diameter full-thickness skin wounds were generated using a dermal biopsy punch (Miltex Instrument Company, York, Pa., USA). Wounded Tcf mice were separated into two study groups: Control group, which received daily intraperitoneal injections of Saline; and Nefopam group, which received daily intraperitoneal injections of 40 mg/kg body weight. At 14 days post-wounding, wound sizes were examined, and wound tissues were collected for RNA and protein extraction and fixed for histological examination.

Human AF Tumour and Normal Fascial Tissue Samples.

Samples of human aggressive fibromatosis tumours were obtained at the time of surgery from the Hospital for Sick Children, Toronto. Tumour tissue and surrounding normal fascial tissue from the same patient were harvested and processed immediately after surgical excision. Tissues were cryopreserved and stored in liquid nitrogen vapour.

Cell Culture Studies.

Primary cell cultures from the human AF tumour and normal fascial tissue samples were established. Monolayer cultures were cultured in DMEM supplemented with 10% fetal bovine serum and maintained at 37° C. in 5% $CO_2$. Cells were divided when confluent and experiments were performed between the first and fifth passages. Prior to experimental studies, cells were seeded overnight and treatment began the following day (Day 0) where cells were treated with vehicle control 0.1% DMSO with or without 250 μm Nefopam prepared in DMEM media.

Cell Viability Assay, Proliferation Assay and Apoptosis Assay were Performed.

Cell viability was measured using the Trypan Blue Dye Exclusion method. Cells were stained with Trypan Blue Dye at a 1:1 ratio, and both live (clear) and dead (blue) cells were accounted for. Proliferation was measured using 5-bromo-2-deoxy-uridine (BrdU) Incorporation assay. After BrdU incubation for 12 hours, cells with incorporated BrdU were identified using rabbit monoclonal anti-BrdU antibody and horse anti-mouse antibody conjugated to Alkaline Phosphatase. Presence of BrdU was detected using Alkaline Phosphatase substrate. Percentage of positively stained nuclei out of total nuclei was analyzed over 10 high-powered fields.

Protein Extraction and Western Blot Analysis.

Tissue samples were washed twice with PBS and lysed with Reporter Gene Assay Lysis Buffer (Roche). Lysates were centrifuged at 16,000×g for 5 minutes to remove cell debris and quantified using the Bicinchoninic Acid (BCA) Protein Assay (Pierce). Equal amounts of total protein were separated by electrophoresis through an SDS-polyacrylamide gel, transferred to a nitrocellulose membrane (Amersham), and immunoblotted overnight at 4° C. with primary antibodies against phosphoGSK3β (Ser 9, rabbit polyclonal, New England Biolabs), β-catenin (mouse monoclonal, Upstate Biotechnology), total GSK3β (mouse monoclonal, Transduction Laboratories), and GAPDH (mouse monoclonal, Upstate Biotechnology). Horseradish Peroxidase (HRP)-tagged secondary antibodies and Enhanced Chemi-Luminescence (Amersham) were used to detect hybridization. Densitometery was performed using the AlphaEaseFC software (Alpha Innotech). Western blotting was performed in triplicates to ensure reproducibility.

Statistical Analysis.

Data in this work are presented as mean±95% confidence intervals. All studies were performed in at least triplicates to ensure reproducibility.

Example 1: Nefopam Treatment Reduces Hyperplastic Wound Cell Viability

Figure 1B:
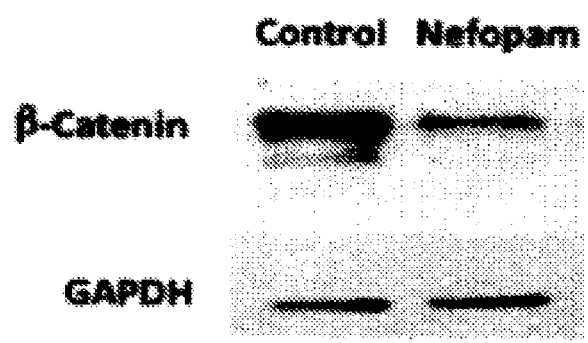
FIG. 1B is a western blot analysis of β-catenin levels in hyperplastic wound cell cultures. Nefopam treatment was shown to substantially reduce β-catenin protein levels compared to DMSO treated controls.

Compounds were screened to identify those that meet two criteria: 1) inhibit cell viability of fibroblasts obtained from hyperplastic wounds which exhibit β-catenin activation; and 2) show little to no effect on normal dermal fibroblast cultures. The biological relevance of the screen was considerable since cells used for the screen were obtained from patients with hyperplastic wounds as well as healthy tissue. The experiments were repeated in triplicate within 96 well plates, with each well containing 4000 cells treated with between 0.1 1.0, or 10 μM of compound or DMSO as a control. The Sulforhodamine B assay (SRB) was used to measure cell viability. Compounds detected within the initial screen underwent further testing using a larger pool of samples, from which Nefopam was identified (see FIG. 1A).

β-catenin levels in cell cultures from hyperplastic scars treated with Nefopam or control were analyzed using Western blot analysis. It was observed that Nefopam substantially reduced the protein level of β-catenin in cell cultures from hyperplastic wounds (see FIG. 1B). GAPDH expression was included as a loading control.

Figure 2:
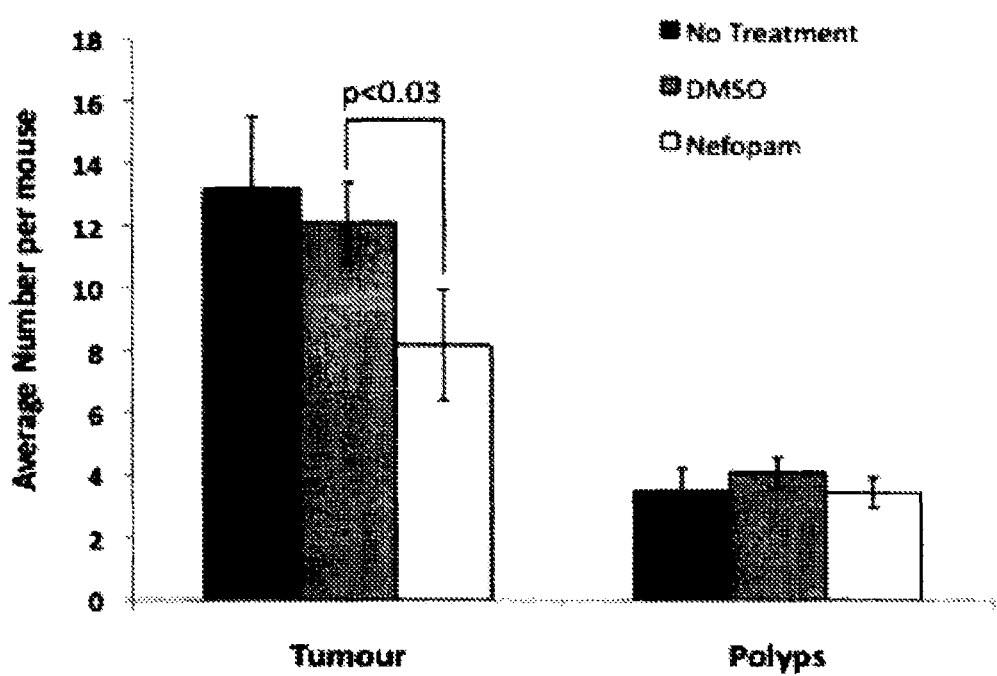
FIG. 2 is a graph comparing the number of aggressive fibromatosis (AF) tumours formed in male Apc+/Apc1638N mice left untreated or treated with Nefopam or DMSO control and illustrating the number of epithelial-derived polyps in the upper gastrointestinal tract under the same treatment. 1) No Treatment (n=11), 2) 0.1% DMSO (n=10), and 3) Nefopam at 40 mg/kg body weight (n=10).

Example 2: Nefopam Decreases the Number of AF Tumours Formed in Apc/Apc1638N Mice It was investigated whether or not Nefopam treatment was able to modulate the phenotype of AF lesions in vivo. The number of AF tumours formed in male Apc/Apc1638N mice treated with Nefopam was significantly reduced compared to the number formed in untreated mice or mice treated with 0.1% DMSO at 6 months of age (8.18±1.77 vs 13.2±2.30 or 12.09±1.31, p<0.03, see FIG. 2). There were no significant differences in the number of epithelial-derived polyps in the upper gastrointestinal tract (see FIG. 2). This shows that Nefopam inhibits tumour initiation and further is specific to mesenchymal cells.

Example 3: Nefopam Decreases β-Catenin Levels in Human AF Tumour Cells

Figure 3A:
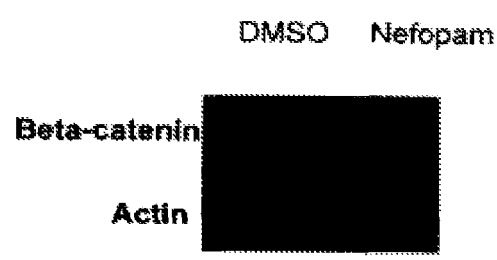
FIG. 3A is a western blot of β-catenin protein levels (92 kDa) in extracts from primary cell cultures derived from human aggressive fibromatosis (AF) tumours (n=5) following treatment for 5 days with one of 0.1% DMSO (control) or Nefopam. β-catenin protein levels were also determined in primary fibroblast cell cultures incubated with Wnt3a with or without Nefopam. Experiments were performed in triplicate. Actin expression is shown as a lysate loading control.
Figure 3B:
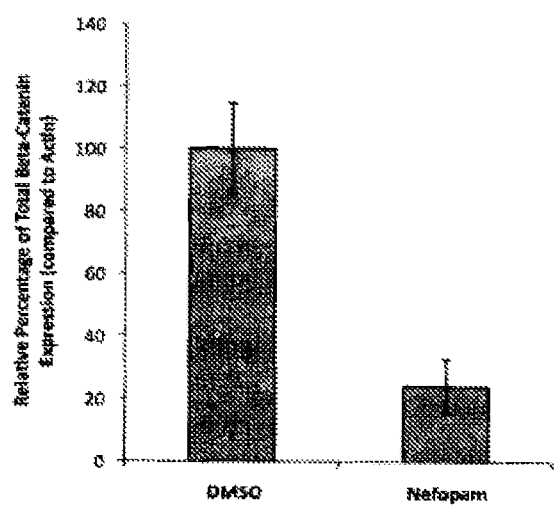
FIG. 3B is a graph of densitometry analysis of protein level data showing a nearly 5-fold decrease in total β-catenin protein levels in cell cultures derived from human AF tumours treated with 0.1% DMSO (control) or Nefopam. Means and 95% confidence intervals are shown. Statistically significant differences (p<0.05) compared to the control are indicated by an asterisk.

AF tumours are characterized by an increase in β-catenin levels. To examine whether Nefopam has the capacity to modulate β-catenin levels, primary cell cultures derived from several human AF tumours were studied. Western blot analysis using an antibody against total β-catenin demonstrated a marked decrease in the amount of protein at size 92 kDa consistent with total β-catenin as a result of Nefopam treatment for 5 days, see FIG. 3A. Densitometry analysis showed nearly a 5-fold decrease in total β-catenin levels in human AF tumour cell cultures treated with Nefopam compared to those treated with 0.1% DMSO (see FIG. 3B). Actin expression was determined as a lysate loading control.

Figure 4A:
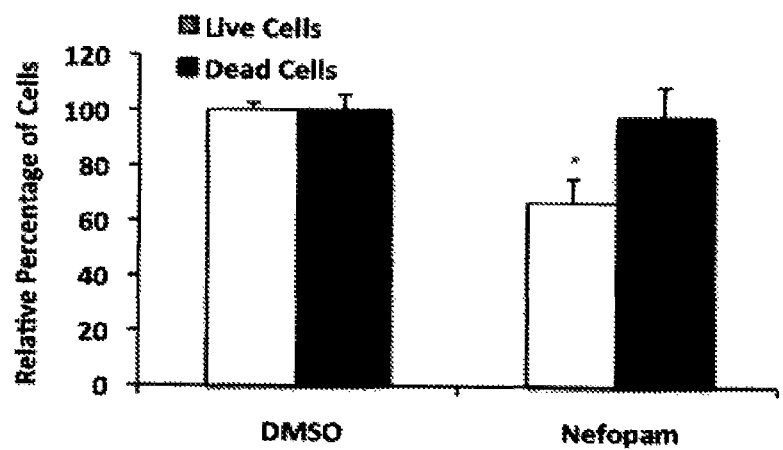
FIG. 4A is a graph showing the means and 95% confidence intervals of cell viability of primary cells derived from human AF tumours treated with DMSO (n=5) or Nefopam (n=5) for 5 days. Cell viability was measured by staining cells with Trypan Blue Dye and counting both live (clear) and dead (blue) cells. Nefopam significantly decreased the number of live cells while the number of dead cells did not change. Statistically significant differences (p<0.05) compared to controls are indicated with an asterisk

Example 4: Nefopam Decreases Cell Viability and Cell Proliferation in Human AF Tumour Cells To determine how Nefopam may modify AF cell behaviour, primary cell cultures derived from several human AF tumours were studied. First, the effects of Nefopam on cell viability in human AF tumours were studied. A significantly smaller number of live cells were observed in human AF tumour cell cultures following Nefopam treatment compared to cultures treated with 0.1% DMSO ($p<0.05$). There were no significant differences in the number of dead cells counted as a result of Nefopam treatment for the tumours ($p<0.05$) (see FIG. 4A).

Figure 4B:
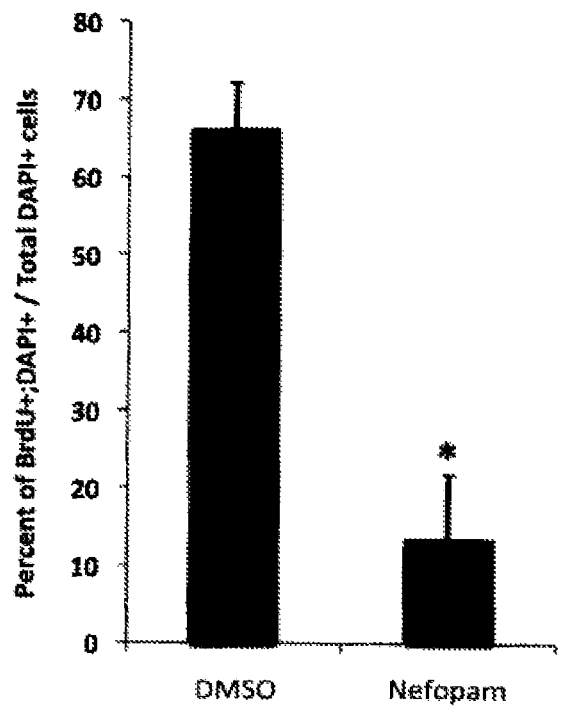
FIG. 4B is a graph showing percent BrdU-positive/DAPI-positive cells compared to total DAPI-positive cells as a measure of proliferation in cultures of primary cells derived from human aggressive fibromatosis tumours (n=2) treated with DMSO or Nefopam in triplicate for 5 days. Nefopam significantly reduces the incorporation of BrdU into cells. The means and 95% confidence intervals are shown. Statistically significant differences (p<0.05) compared to the control are indicated by asterisk.

Upon demonstrating that β-catenin levels are involved in the regulation of the rate of proliferation in mesenchymal cells, the effects of Nefopam on proliferation in primary cell cultures were investigated. Using the BrdU incorporation assay, the percentage of BrdU+/DAPI+ cells compared to total DAPI+ cells was measured. It was observed that Nefopam-treated human AF tumours contained significantly fewer proliferating cells as determined by BrdU incorporation ($p<0.05$, see FIG. 4B).

Together, these results show that Nefopam preferentially inhibits the number of viable AF cells by reducing the rate of proliferation.

Figure 5A:
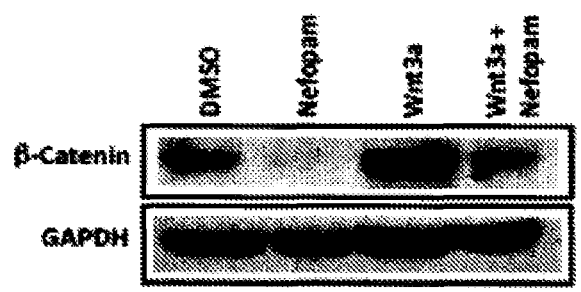
FIG. 5A shows western blot analysis of lysates extracted from immortalized human fibroblast cells. A significant decrease in total β-catenin protein levels in cells treated with Nefopam compared to cells treated with DMSO was observed. GAPDH expression is shown as a lysate loading control.
Figure 5B:
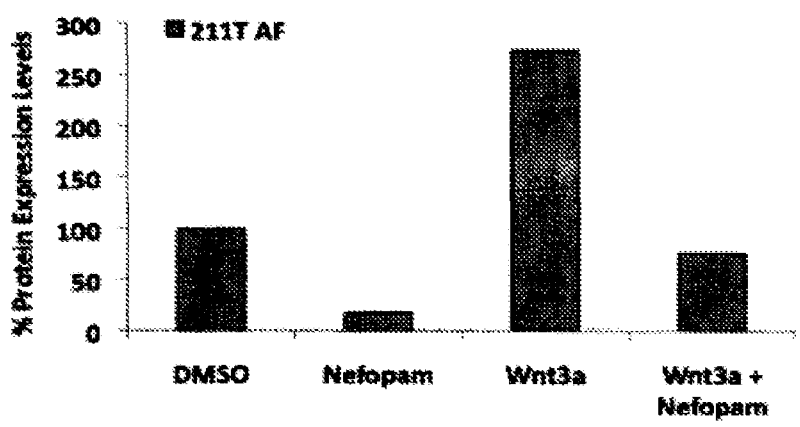
FIG. 5B is a graph of densitometry data corresponding to western blot data of FIG. 5A.

Example 5: Nefopam Decreases β-Catenin Levels in Primary Human Fibroblast Cell Cultures Hyperplastic wounds are characterized by elevated β-catenin levels during the proliferative phase. The data described herein show that Nefopam has the capacity to modulate β-catenin levels particularly in mesenchymal-derived cells. To confirm that Nefopam can modulate β-catenin levels in mesenchymal cells, immortalized human fibroblast cells were treated with Nefopam (see FIG. 5A). Nefopam treatment resulted in an approximately 4-fold decrease in total β-catenin levels in primary human fibroblast cell cultures compared to cultures treated with 0.1% DMSO as determined by densitometry analysis ($p<0.05$, see FIG. 5B). Additional controls included in the experiments were Wnt3a treatment of cells (known to increase β-catenin expression) and effects of Nefopam on cells treated with Wnt3a.

Figure 6A:
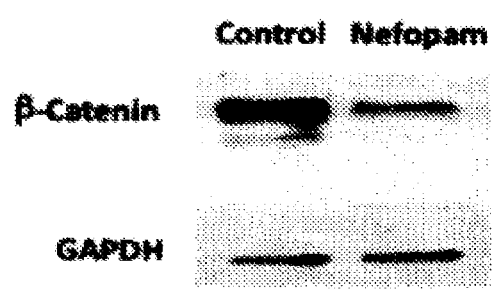
FIG. 6A is a western blot analysis of β-catenin protein levels in cell cultures from Tcf mice wounds 14 days post-wounding. GAPDH expression is shown as lysate loading control.

Example 6: Systemic Nefopam Decreases β-Catenin Levels and Wound Sizes in Tcf Mice Next, to examine the effects of Nefopam on β-catenin levels during wound healing, wounded tissue from Tcf mice were studied. Cutaneous wounds were generated using a biopsy punch procedure resulting in a 4 mm diameter full thickness circular wound. Scale is in mm units. Western blotting using an antibody against total β-catenin (see FIG. 6A) demonstrated a decrease in β-catenin levels in cells cultured from wounds derived from Tcf mice treated with Nefopam compared to the control group 14 days post-wounding.

Figure 6B:
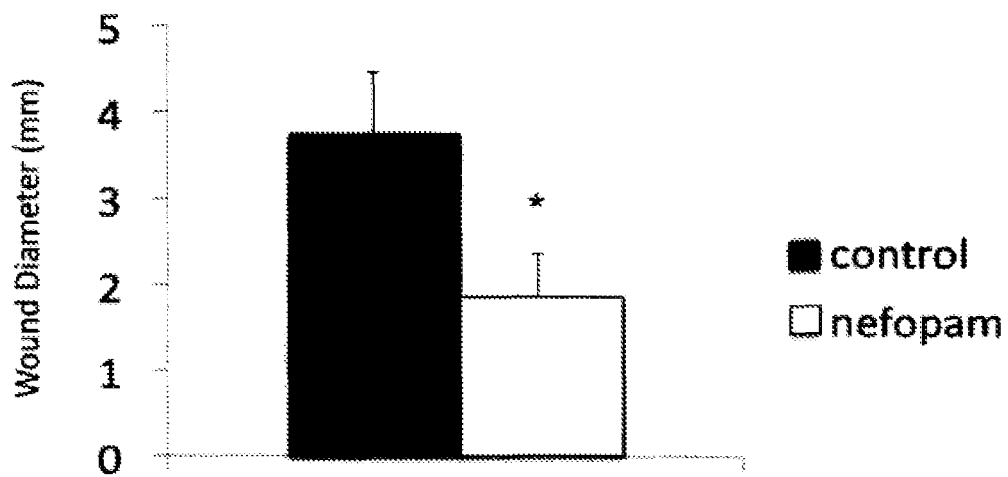
FIG. 6B is a graph of normal scar size in mice subjected to full thickness circular wounds following treatment with either Nefopam formulated with a carrier (Nefopam) or carrier alone (control) administered systemically as 40 mg/kg daily for two weeks. The graph shows the mean and 95% confidence interval for the diameter of the surface area of a cutaneous wound generated using a 4 mm biopsy punch. The diameter of the wound is significantly smaller following Nefopam treatment compared to control treatment (asterisk indicates a significant difference).

Furthermore, examination of the wounds upon autopsy showed Nefopam-treated mice had scars significantly smaller in diameter compared to carrier (saline) treated controls at day 14 post-wounding (asterisk indicates a significant difference, $p<0.001$) (see FIG. 6B).

Example 7: Systemic Nefopam Reduces Hyperplastic Scar Size Induced by TGF-β

Figure 7:
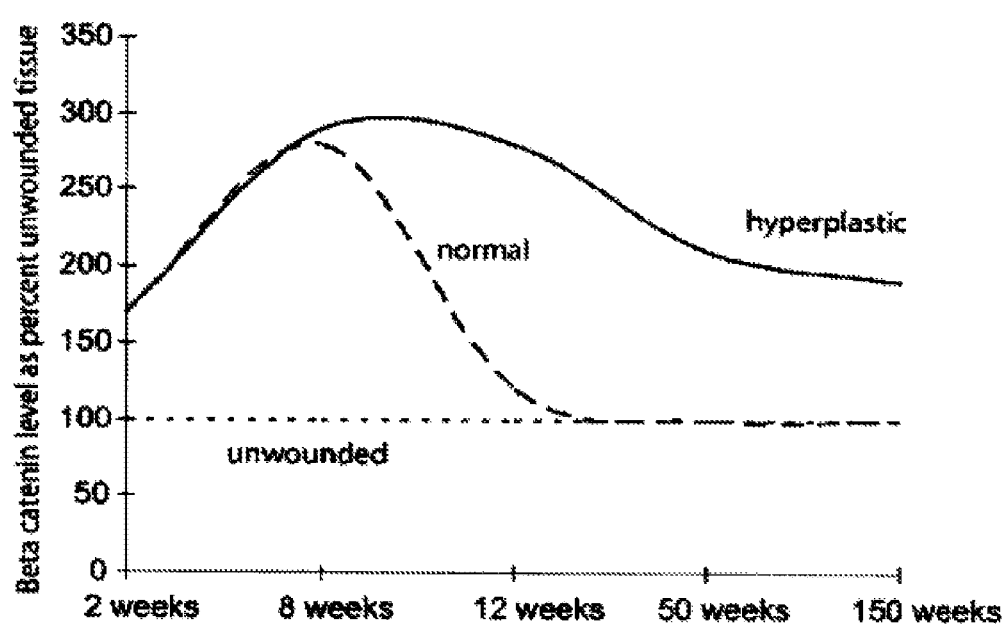
FIG. 7 is a line graph indicating relative β-catenin protein levels over time (measured in weeks) during normal wound healing (normal) and in hyperplastic wounds (hyperplastic) compared to unwounded tissue. The normal pattern of rise and fall of β-catenin protein levels during normal wound healing is deregulated in hyperplastic wounds, which exhibit a significantly prolonged duration of elevated β-catenin protein levels.

It is known that β-catenin protein levels increase during the early stages of wound healing then fall through later stages relative to unwounded tissue. The normal rise and fall of β-catenin protein levels are deregulated during hyperplastic wound healing where significantly prolonged elevated levels of β-catenin are observed (see FIG. 7).

Figure 8:
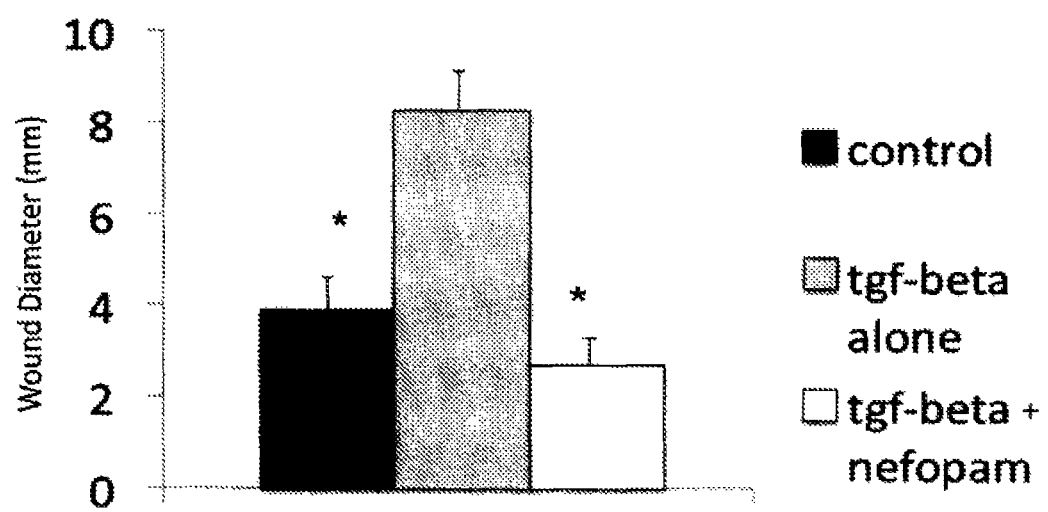
FIG. 8 is a graph of the mean and 95% confidence interval for the diameter of the surface area of cutaneous hyperplastic scars four weeks post-wounding. 4 mm diameter full thickness circular wounds were generated using a biopsy punch. Wound diameter is given in mm. An asterisk indicates statistically significant differences in scar size noted when compared to treatment with TGF-β (p<0.01), where TGF-β injection at the time of wounding is known to cause hyperplastic scars of increased size.

Following drug screen studies, effects of Nefopam were tested in vivo using mice. Both oral and intraperitoneal administration routes were evaluated (40 mg/kg body weight, daily; 0.1% DMSO as control). In both administration routes, Nefopam was identified in the scrum as detected using HPLC (data not shown). 4 mm full thickness punch wounds were made in the skin, and Nefopam or control was administered daily after wounding. To determine if Nefopam is effective in treating hyperplastic scars, a mouse hyperplastic scar model, in which TGF-β is injected prior to wounding resulting in a hyperplastic scar, was used. Importantly, the same Nefopam treatment regimen, as described above, resulted in smaller scars as compared to control scars not treated with TGF-β (see FIG. 8). Thus, Nefopam is able to reduce scar size in both hyperplastic and normal wound repair.

Example 8: Various Carriers can be Used for Topical Delivery of Nefopam

Figure 9:
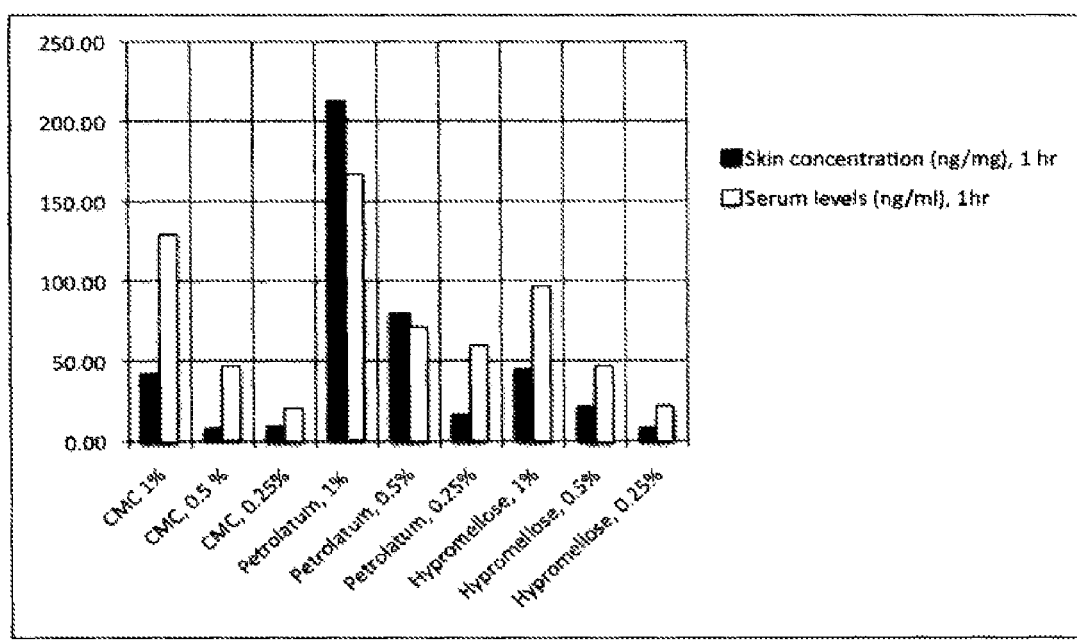
FIG. 9 is a graph of varying concentration Nefopam topical formulations in three different carriers: carboxymethylcellulose (CMC), petrolatum, and hypromellose. The three carriers were tested in vivo in a mouse model to determine the formulation most effective in delivering Nefopam through the skin. Petrolatum-based carrier formulations demonstrated enhanced Nefopam release properties as determined by measurement of Nefopam levels in the skin and serum.

For skin wounds, an ideal product is a topical formulation of Nefopam. Topical Nefopam formulations using the following carriers were prepared and evaluated: carboxymethylcellulose (CMC), petrolatum, and hypromellose. The three carriers were tested in vivo to determine the formulation effective to deliver Nefopam through the skin. The results are illustrated in FIG. 9.

Example 9: Topical Nefopam Decreases Normal Scar Size in Mice

Cutaneous wounds were generated in Tcf mice using the biopsy punch procedure described above. 6 mm diameter full thickness punch wounds were treated topically with either control cream of 1% Nefopam cream twice daily for up to 21 days. It was observed that Nefopam treatment resulted in a reduction in scar size by approximately one third compared to controls. Table 1 indicates the average normal wound size (measured in mm) in a mouse model at day 0 and following 21 days of daily topical administration of either 1% Nefopam cream formulated in petrolatum carrier or carrier alone control cream. Averages are provided for 4 wounds per group.

TABLE 1

|  |  | Day 0 | Day 21 |
| --- | --- | --- | --- |
| Control | Average size of wound (mm) | 6 | 3.116666667 |
| 1% nefopam | Average size of wound (mm) | 6 | 2.02 |

Figure 10:
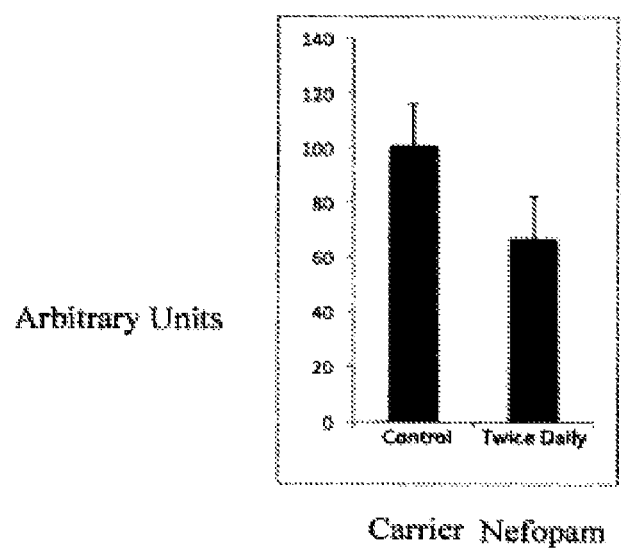
FIG. 10 is a graph of relative scar surface area measured in arbitrary units (the scar size upon wounding is considered as 100 arbitrary units). Full thickness puncture wounds 4 mm in diameter were treated topically with either carrier control cream or 1% Nefopam cream formulated in petrolatum carrier twice daily for 14 days. The data represent an average of 10 wounds per treatment with standard deviation.

4 mm punch wounds were generated in Tcf mice which were then treated topically with one of 1% Nefopam cream or control cream twice daily for 14 days. The surface areas of scars formed after 14 days of treatment were measured using arbitrary units, where 100 arbitrary units represents the control cream treatment. Ten wounds were measured for each treatment and data presented as mean and standard deviation. It was observed that scars in mice receiving Nefopam treatment were significantly smaller than those subjected to control treatment (p<0.05) where control treatment is 0% Nefopam (see FIG. 10).

Example 10: Various Excipients can be Used for Topical Delivery of Nefopam

According to certain embodiments of the invention the dosage form to be used for topical applications is BID 1% Nefopam HCl cream (oil in water emulsion (O/W)). In these embodiments the application of the inventive compounds may start approximately 5-7 days post-surgery and conclude at approximately 30 days. In certain embodiments, application of the inventive compounds to the wound is by the patient. Therefore a preservative system is provided. Nefopam HCl is hydrophilic but the hydrochloride salt form has improved aqueous solubility and contains a chiral centre and it is believed that there are two enantiomers in a 50:50 ratio. The ideal pH for solutions of Nefopam HCl according to the invention is 5.2 to 5.4. For skin wounds of humans, an ideal product must be stable, spreadable, penetrate well, and ideally have low odor. Topical Nefopam formulations using a variety of combinations of excipients are disclosed herein.

Example 11: Topical Formulation with Transcutol® P and without Calcium Gluconate Table 2 below provides the ingredient concentrations (mg/g) of one topical formulation of Nefopam HCl 1% cream according to the invention.

TABLE 2

| Ingredients | mg/g | mg/g |
| --- | --- | --- |
| Nefopam HCl (as free base) | 10.00 | 10.00 |
| Transcutol ® P | 30.00 | 45.00 |
| Cetyl Alcohol NF | 40.00 | 40.00 |
| Stearyl Alcohol NF | 30.00 | 30.00 |
| Liposorb ® S-20 (Polysorbate 60 NF) | 40.00 | 40.00 |
| Propylparaben NF | 0.50 | 0.50 |
| Lexol (Isopropyl Myristate NF) | 22.50 | 15.00 |
| Purified Water, USP | 818.50 | 810.00 |
| Methylparaben NF | 1.00 | 1.00 |
| Calcium Gluconate NF | — | — |
| EDTA | 0.02 | 0.02 |
| Purified Water, USP for 10% Solution NaOH | 4.50* | 4.50* |
| Sodium Hydroxide NF, qs to 5.0 to 5.6 | 0.50* | 0.50* |
| Total (mg) | 1000.00 | 1000.00 |

*The quantity entered is the actual quantity added to the batch to achieve an approximate pH of 5.3. pH of each batch was taken at approximately 56° C. to 60° C.

General processing directions with Transcutol® and without calcium gluconate:
1. Load cetyl alcohol, stearyl alcohol, polysorbate 60, and isopropyl myristate into a suitable jacketed cream/ointment processing kettle. Heat to 65° C. to 70° C. while mixing.
2. Load Propylparaben and mix to ensure complete dissolution. Maintain the temperature at 65° C. to 70° C.
3. Load Transcutol® into a stainless steel container. Heat to 60° C. to 65° C. Add Nefopam HCl while stirring. Mix to form a slurry. After approximately 10 minutes of stirring, add to Step 2 while mixing. The container will be rinsed with purified water in commercial or GMP processing to affect a quantitative transfer.
4. Add purified water into a heated, stainless steel tank, equipped with a mixer. Stir while heating to 65 to 70° C. Add EDTA and mix to dissolve. Add methylparaben and mix to dissolve. Maintain the temperature at 65° C. to 70° C. Maintain the temperature at 65° C. to 70° C.
5. Transfer step 3 into step 2. Qs to 99%. Homogenize and mix for 30 minutes while maintaining the temperature at 65° C. to 70° C. while imparting a vacuum of −0.4 to −0.6 Atm.
6. Adjust the pH to 5.0 to 5.6 with 1N NaOH. Measured at 25° C. Ensure complete homogeneity after the addition of the pH adjusting agent by homogenizing and mixing for 5 minutes after each addition. Qs with purified water if necessary.
7. Cool, while mixing and homogenizing, to 55° C. to 58° C. At 55° C., turn off the homogenizer. Maintain the vacuum while slowly mixing and cooling to less than 30° C. Fill into 50 mL glass jars, cap and label.

Example 12: Topical Formulation with Transcutol® and with Calcium Gluconate

Table 3 below provides the ingredient concentrations (mg/g) of one topical formulation of Nefopam HCl 1% cream according to the invention.

TABLE 3

| Ingredients | mg/g |
| --- | --- |
| Nefopam HCl (as free base) | 10.00 |
| Transcutol ® P | 30.00 |
| Cetyl Alcohol NF | 40.00 |
| Stearyl Alcohol NF | 30.00 |
| Liposorb ® S-20 (Polysorbate 60 NF) | 40.00 |
| Propylparaben NF | 0.50 |
| Lexol (Isopropyl Myristate NF) | 22.50 |
| Purified Water, USP | 806.50 |
| Methylparaben NF | 1.00 |
| Calcium Gluconate NF | 5.00 |
| EDTA | 0.02 |
| Purified Water, USP for 10% Solution NaOH | 4.50* |
| Sodium Hydroxide NF, qs to 5.0 to 5.6 | 0.50* |
| Total (mg) | 1000.00 |

*The quantity entered is the actual quantity added to the batch to achieve an approximate pH of 5.3. pH of each batch was taken at approximately 56° C. to 60° C.

General Processing Directions with Transcutol® and with Calcium Gluconate:
1. Load cetyl alcohol, stearyl alcohol, polysorbate 60, and, isopropyl myristate into a suitable jacketed cream/ointment processing kettle. Heat to 65° C. to 70° C. while mixing.
2. Load propylparaben and mix to ensure complete dissolution. Maintain the temperature at 65° C. to 70° C.
3. Load Transcutol® into a stainless steel container. Heat to 60° C. to 65° C. Add Nefopam HCl while stirring. Mix to form a slurry. After approximately 10 minutes of stirring, add to Step 2 while mixing. The container will be rinsed with purified water in commercial or GMP processing to affect a quantitative transfer.
4. Add purified water into a heated, stainless steel tank, equipped with a mixer. Stir while heating to 65° C. to 70° C. Add methylparaben and mix to dissolve. Add calcium gluconate and mix to dissolve. Maintain the temperature at 65° C. to 70° C. Maintain the temperature at 65° C. to 70° C.
5. Transfer step 3 into step 2. Qs to 99%. Homogenize and mix for 30 minutes while maintaining the temperature at 65° C. to 70° C. while imparting a vacuum of −0.4 to −0.6 Atm.
6. Adjust the pH to 5.0 to 5.6 with 10% NaOH. Measured at 55° C. to 65° C. Ensure complete homogeneity after the addition of the pH adjusting agent by homogenizing and mixing for 5 minutes after each addition. Qs with purified water if necessary.

7. Cool, while mixing and homogenizing, to 55° C. At 55° C., turn off the homogenizer. Maintain the vacuum while slowly mixing and cooling to less than 30° C. Fill into 50 mL glass jars, cap and label.

Example 13: Topical Formulation without Transcutol® and without Calcium Gluconate Table 4 below provides the ingredient concentrations (mg/g) of one topical formulation of Nefopam HCl 1% cream according to the invention.

TABLE 4

| Ingredients | mg/g |
| --- | --- |
| Nefopam HCl (as free base) | 10.00 |
| Transcutol ® P | — |
| Cetyl Alcohol NF | 40.00 |
| Stearyl Alcohol NF | 30.00 |
| Liposorb ® S-20 (Polysorbate 60 NF) | 40.00 |
| Propyl Paraben NF | 0.50 |
| Lexol (Isopropyl Myristate NF) | 22.50 |
| Purified Water, USP | 838.50 |
| Methyl Paraben NF | 1.00 |
| Calcium Gluconate NF | — |

TABLE 4-continued

| Ingredients | mg/g |
| --- | --- |
| EDTA | 0.02 |
| Purified Water, USP for 10% Solution NaOH | 4.50* |
| Sodium Hydroxide NF, qs to 5.0 to 5.6 | 0.50* |
| Total (mg) | 1000.00 |

*The quantity entered is the actual quantity added to the batch to achieve an approximate pH of 5.3. pH of each batch was taken at approximately 56° C. to 60° C.

General processing directions without Transcutol® and without calcium gluconate:

1. Load cetyl alcohol, stearyl alcohol, polysorbate 60, and isopropyl myristate into a suitable jacketed cream/ointment processing kettle. Heat to 65° C. to 70° C. while mixing.
2. Load propylparaben into Step 1. Mix to ensure complete dissolution. Maintain the temperature at 65° C. to 70° C.
3. Add 409.25 g of purified water into a heated, stainless steel tank equipped with a mixer. Stir while heating to 65° C. to 70° C. Add EDTA and mix to dissolve. Add methylparaben and mix to dissolve. Maintain the temperature at 65° C. to 70° C. Add Nefopam HCl while stirring. Mix until dissolved. Maintain the temperature at 65° C. to 70° C.
4. Transfer Step 3 into Step 2. Qs to 99%. Homogenize and mix for 30 minutes while maintaining the temperature at 65 to 7° C. while imparting a vacuum of −0.4 to −0.6 Atm.
5. Adjust the pH to 5.0 to 5.6 with 1N NaOH. Measured at 25° C. Ensure complete homogeneity after the addition of the pH adjusting agent by homogenizing and mixing for 5 minutes after each addition. Qs with purified water if necessary.
6. Cool, while mixing and homogenizing, to 55° C. At 55° C., turn off the homogenizer. Maintain the vacuum while slowly mixing and cooling to less than 30° C. Fill into 50 mL glass jars, cap and label.

Example 14: Comparison of the Physical Aspects of the Cream Formulations

The table below compares the results of the physical tests of the four (4) formulae.

TABLE 5

| Test | Example 11 with low Transcutol ® P | Example 11 with high Transcutol ® P | Example 12 | Example 13 |
| --- | --- | --- | --- | --- |
| Appearance | White, shiny smooth cream. Medium-low viscosity** | White, shiny smooth cream. Medium viscosity** | White, shiny smooth cream. Medium viscosity** | White, shiny smooth cream. Medium viscosity** |
| Microscopic appearance (100X) | Ultrafine, well dispersed emulsion. No evidence of undissolved API. | Ultrafine, well dispersed emulsion. No evidence of undissolved API. | Ultrafine, well dispersed emulsion. No evidence of undissolved API. | Ultrafine, well dispersed emulsion. No evidence of undissolved API. |
| pH 5.0-5.6*** | ≈5.3 | ≈5.3 | ≈5.3 | ≈5.3 |

**The viscosity determination is subjective and is based on moving a spatula through the cream to determine resistance.
***The pH was taken with a pH meter, calibrated at pH 4.0 and 7.0. The temperature of the cream was ≈60° C. during the testing. The pH meter was adjusted to 60° C. for the pH testing.

Example 15: Topical Treatment of Wounds with 1% Nefopam Cream in Duroc Pigs

The efficacy of a 1% Nefopam cream disclosed in Example 11 (30 mg Transcutol® P) applied daily to 2×2 cm excisional wounds and 2 cm incisional wounds when compared to cream vehicle alone (control). The topical formulation used in this Example was optimization to enhance stability and delivery of the Nefopam. The effects on wound repair and scar formation were quantified.

Four Duroc pigs (two males and two females) weighing 6-8 kg were used for this Example. Two 2×2 cm wounds were generated on the back of each pig, one wound on each side. The wounds were generated by excising a full thickness section of skin (to the muscle layer). Half of the pigs (2 pigs, 4 wounds) were treated daily with cream vehicle (controls) while the other half (2 pigs, 4 wounds) were treated daily with 1% Nefopam cream. Meloxicam (analgesic; 5 mg/ml at 0.4 mg/kg IM) and Penicillin G (antibiotic; 300,000 UI/ml at 1 ml/20 kg IM) were administered to each pig after surgery. One week later, further surgery was performed on these pigs to generate 2 cm incisional slit wounds (one wound on each side of the pig for a total of two incisional wounds per pig). These were generated using a scalpel, incising deep to the muscle layer. Both the 2×2 cm excisional wounds and the 2 cm incisional wounds were monitored and photographs taken each week to document healing. The scar area was quantified using the Alpha-EaseFC 4.0 program. All pigs (Nefopam treated and controls) were monitored for 4 weeks in the case of post-excisional wounding and 3 weeks in the case of post-incisional wounding.

At four weeks post-excisional wounding, the pigs were sacrificed and the wound tissues were excised and fixed in 10% formalin for histological analyses. Scar size was measured from the histological sections using Masson-Trichrome stained sections cut across the wound perpendicular to the skin. Serial sections were cut across the scar to identify the widest diameter of each scar (mid aspect of the scar), and this section was used to measure scar size. An observer blinded to the treatment measured the scar size.

Table 6 below is a summary of histology measurements for 2×2 cm excisional wounds on pigs treated with 1% Nefopam cream according to Example 11 vs. control at day 28 post-wounding; n=2 pigs/group.

TABLE 6

|  |  | Control | 1% Nefopam Cream |
|---|---|---|---|
| Day 28 | Average | 52.7 | 34.9 |
|  | Standard Deviation | 10.8 | 3.9 |
|  | 95% Confidence Limit | 4.5 | 1.0 |
|  | T test to control | N/A | 9.6E−08 |

Table 7 below is a summary of histology measurements for 2 cm incisional wounds on pigs treated with 1% Nefopam cream according to Example 11 vs. control at day 21 post-wounding; n=2 pigs/group.

TABLE 7

|  |  | Control | 1% Nefopam Cream |
|---|---|---|---|
| Day 21 | Average | 39.6 | 24.4 |
|  | Standard Deviation | 6.9 | 3.3 |
|  | 95% Confidence Limit | 3.0 | 1.4 |
|  | T test to control | N/A | 1.3E−09 |

The excisional and incisional wound area and scar size data derived both from the weekly photographic measurements of the scars and measurements from histology sections, respectively, indicated that there was a significant difference in scar size between Duroc pigs treated with 1% Nefopam cream and those treated with vehicle cream (control). Specifically, the surface scar images showed a markedly reduced scar size through the duration of wound repair of the 2×2 cm excisional wounds and the 2 cm incisional wounds over 28 days. Additionally, the scar size as determined from the final histological sections was significantly smaller at Day 28 for the 2×2 cm excisional wounds and at Day 21 for the 2 cm incisional wounds after Nefopam treatment compared to control.

The results of these studies on wound repair and scar formation in the Duroc pig model subjected to excisional and incisional wounds and treated with 1% Nefopam cream according to Example 11 or control confirmed the results from the earlier studies of wound repair and scar formation following Nefopam treatment (wild-type mouse model (see Example 9) and pigs treated with initial cream formulations).

Specifically, the excisional and incisional wound studies in Duroc pigs demonstrate that there is a significant improvement in wound repair and reduction in scar size formation following daily treatment with 1% Nefopam cream.

Example 16: Acne Treatment

According to certain embodiments of the invention, the cream dosage form is used to reduce scarring resulting from acne. In this example, 1% Nefopam HCl cream is applied twice daily directly to the wounded area for 30 days or until the wound has disappeared.

Example 17: Treating a Human Wound with a Nefopam Cream

A patient sustained a cut from a saw approximately 1 cm in length on a knuckle. The wound was closed with non-dissolving sutures. On day 4 after the injury, treatment with 1% Nefopam cream disclosed in Example 11 (30 mg Transcutol® P) was initiated. The cream was applied twice daily for 21 days. The sutures were removed after 9 days. The patient continued all of his regular daily activities. There were no adverse effects from the treatment and the scar from the wound is virtually undetectable.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

Any publications, patents and patent applications referred to herein are incorporated by reference in their entirety to the same extent as if each individual publication, patent or patent application was specifically and individually indicated to be incorporated by reference in its entirety.

We claim:

1. A method of treating a mammal suffering from a fibroproliferative disorder selected from the group consisting of hyperplastic wounding, cuts, acne and aggressive fibromatosis tumors in the upper gastrointestinal tract, comprising administering to said mammal suffering from a fibroproliferative disorder selected from the group consisting of hyperplastic wounding, cuts, acne and aggressive fibromatosis tumors in the upper gastrointestinal tract, a composition comprising a nefopam compound selected from nefopam, or a functionally equivalent salt or solvate thereof.

2. The method of claim 1, wherein the fibroproliferative disorder is characterized by excessive proliferation of mesenchymal fibroblast-like spindle cells.

3. The method of claim 1, wherein the fibroproliferative disorder comprises hyperplastic wounding.

4. The method of claim 1, wherein the fibroproliferative disorder comprises aggressive fibromatosis.

* * * * *